United States Patent
Gui

(10) Patent No.: US 9,489,817 B2
(45) Date of Patent: Nov. 8, 2016

(54) INFRARED SENSING OF EYE AND EYELID MOVEMENTS TO DETECT DROWSINESS

(71) Applicant: Vigo Technologies Inc., San Francisco, CA (US)

(72) Inventor: Jason Gui, San Francisco, CA (US)

(73) Assignee: Vigo Technologies, Inc., San Francisco, CA (US)

( * ) Notice: Subject to any disclaimer, the term of this patent is extended or adjusted under 35 U.S.C. 154(b) by 0 days.

(21) Appl. No.: 14/608,195

(22) Filed: Jan. 29, 2015

(65) Prior Publication Data

US 2016/0225244 A1    Aug. 4, 2016

(51) Int. Cl.
| | |
|---|---|
| G08B 23/00 | (2006.01) |
| G08B 21/06 | (2006.01) |
| G06K 9/00 | (2006.01) |
| A61B 5/11 | (2006.01) |
| A61B 3/113 | (2006.01) |

(52) U.S. Cl.
CPC ............... *G08B 21/06* (2013.01); *A61B 3/113* (2013.01); *A61B 5/1103* (2013.01); *G06K 9/00604* (2013.01)

(58) Field of Classification Search
CPC ...... A61B 3/113; A61B 5/1103; G08B 21/06
USPC ....... 340/575, 576, 573.1; 382/117; 600/558
See application file for complete search history.

(56) References Cited

U.S. PATENT DOCUMENTS

| | | | | |
|---|---|---|---|---|
| 6,542,081 | B2 * | 4/2003 | Torch | A61B 3/0066 340/575 |
| 7,280,678 | B2 * | 10/2007 | Haven | A61B 3/113 382/117 |
| 7,486,386 | B1 * | 2/2009 | Holcombe | G01C 3/08 356/4.01 |
| 7,488,294 | B2 * | 2/2009 | Torch | A61B 3/0066 600/558 |
| 7,515,054 | B2 * | 4/2009 | Torch | A61B 3/0066 340/573.1 |
| RE41,376 | E * | 6/2010 | Torch | A61B 3/0066 340/573.1 |
| RE42,471 | E * | 6/2011 | Torch | A61B 3/0066 340/573.1 |
| 7,956,756 | B2 * | 6/2011 | Kubey | A61B 3/113 340/573.1 |
| 8,314,707 | B2 * | 11/2012 | Kobetski | A61B 5/18 340/575 |
| 8,446,470 | B2 * | 5/2013 | Lu | H04N 5/2258 348/148 |

\* cited by examiner

*Primary Examiner* — John A Tweel, Jr.
(74) *Attorney, Agent, or Firm* — Chia-Hsin Suen

(57) ABSTRACT

The disclosed embodiments provide a head-mounted device. The head-mounted device includes a sensing apparatus, which contains a first infrared emitter and a second infrared emitter positioned below the first infrared emitter, wherein the first and second infrared emitters alternate emission of infrared pulses at an eye of a user. The sensing apparatus also includes a first infrared detector that produces a first measurement of a reflection of the infrared pulses from the eye of the user. The head-mounted device also includes a processing apparatus that analyzes the first measurement from the first infrared detector to characterize an eyelid movement of the user.

20 Claims, 6 Drawing Sheets

INFRARED SENSING OF EYE AND EYELID MOVEMENTS TO DETECT DROWSINESS

BACKGROUND

1. Field

The disclosure relates to techniques for detecting drowsiness. More specifically, the disclosure relates to techniques for infrared sensing of eye and eyelid movements to detect drowsiness.

2. Related Art

Drowsiness is a common problem that can result in loss of productivity, accidents, and reduced revenue. For example, shift workers and long-distance truck drivers may be susceptible to a significantly increased risk of workplace injuries and traffic accidents resulting from drowsiness. Similarly, students in a classroom may experience reduced levels of alertness that interfere with the students' ability to learn or participate in a classroom discussion. Consequently, effective and safe execution of tasks may be improved by detecting and managing fatigue and drowsiness in users performing the tasks.

SUMMARY

The disclosed embodiments provide a head-mounted device. The head-mounted device includes a sensing apparatus, which contains a first infrared emitter and a second infrared emitter positioned below the first infrared emitter, wherein the first and second infrared emitters alternate emission of infrared pulses at an eye of a user. The sensing apparatus also includes a first infrared detector that produces a first measurement of a reflection of the infrared pulses from the eye of the user. The head-mounted device also includes a processing apparatus that analyzes the first measurement from the first infrared detector to characterize an eyelid movement of the user.

In one or more embodiments, the sensing apparatus also includes a third infrared emitter positioned to a side of the first or second infrared emitters, and the processing apparatus also analyzes the first measurement from the first infrared detector to detect an eye movement of the user.

In one or more embodiments, the sensing apparatus also includes a second infrared detector positioned to a side of the first infrared detector, wherein the second infrared detector produces a second measurement of the reflection of the infrared signal from the eye of the user. In these embodiments, the processing apparatus also analyzes the second measurement from the second infrared detector detect an eye movement of the user.

In one or more embodiments, the processing apparatus also determines a level of alertness in the user based on the characterized eyelid movement of the user.

In one or more embodiments, the head-mounted device also includes an alert-generation mechanism that generates an alert when the level of the alertness in the user drops below a threshold.

In one or more embodiments, the alert includes an audio alert, a visual alert, a vibration, an action on a portable electronic device paired with the head-mounted device, an electrical stimulus, and/or a chemical stimulus.

In one or more embodiments, the characterized eyelid movement includes a blink rate, a blink duration, a closing amplitude velocity ratio, an opening amplitude velocity ratio, a percentage of eyelid closure (PERCLOS), a closing duration, a closure duration, and/or a reopening duration.

In one or more embodiments, analyzing the first measurement from the first infrared detector to characterize the eyelid movement of the user includes:
 (i) identifying a closing of the eyelid of the user from an increase in the first measurement of the reflected infrared pulses from the first infrared emitter, followed by an increase in the first measurement of the reflected infrared pulses from the second infrared emitter; and
 (ii) identifying an opening of the eyelid of the user from a decrease in the first measurement of the reflected infrared pulses from the second infrared emitter, followed by a decrease in the first measurement of the reflected infrared pulses from the first infrared emitter.

In one or more embodiments, the head-mounted device is a headset, a head-mounted display, a helmet-mounted device, a hat-mounted device, eyeglasses, safety glasses, and/or an eyewear device.

BRIEF DESCRIPTION OF THE DRAWINGS

In the figures, like elements are denoted by like reference numerals.

DETAILED DESCRIPTION

In the following detailed description, numerous specific details are set forth to provide a thorough understanding of the disclosed embodiments. However, it will be apparent to those skilled in the art that the disclosed embodiments may be practiced without these specific details. In other instances, well-known features have not been described in detail to avoid unnecessarily complicating the description.

Methods, structures, apparatuses, modules, and/or other components described herein may be enabled and operated using hardware circuitry, including but not limited to transistors, logic gates, and/or electrical circuits such as application-specific integrated circuits (ASICs), field-programmable gate arrays (FPGAs), digital signal processors (DSPs), and/or other dedicated or shared processors now known or later developed. Such components may also be provided using firmware, software, and/or a combination of hardware, firmware, and/or software.

The operations, methods, and processes disclosed herein may be embodied as code and/or data, which may be stored on a non-transitory computer-readable storage medium for use by a computer system. The computer-readable storage medium may correspond to volatile memory, non-volatile memory, hard disk drives (HDDs), solid-state drives (SSDs), hybrid disk drives (HDDs), magnetic tape, compact discs (CDs), digital video discs (DVDs), and/or other media capable of storing code and/or data now known or later developed. When the computer system reads and executes the code and/or data stored on the computer-readable storage medium, the computer system performs the methods and processes embodied in the code and/or data.

Figure 1:
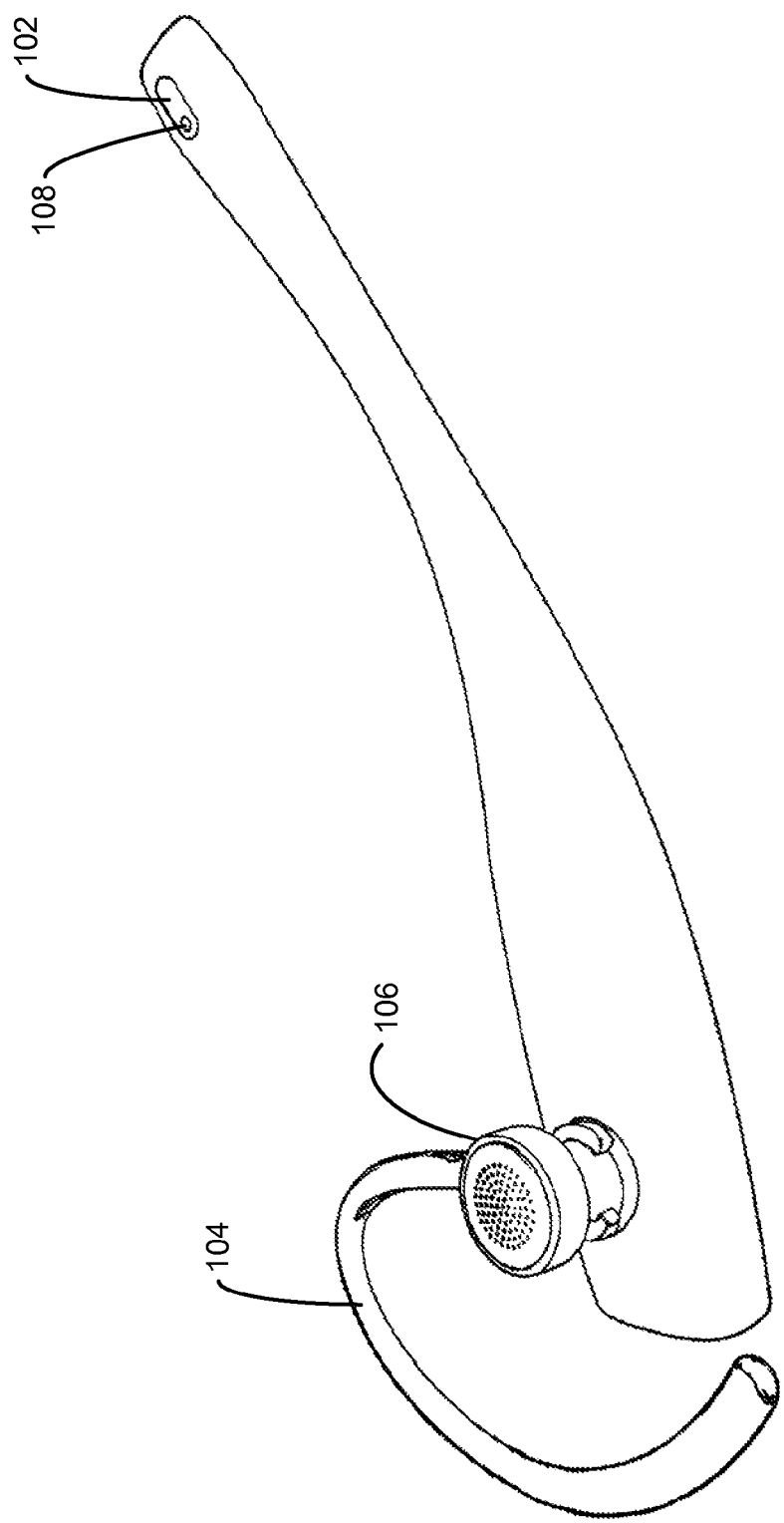
FIG. 1 shows a head-mounted device in accordance with one or more embodiments.

The disclosed embodiments relate to a head-mounted device for detecting drowsiness. As shown in FIG. 1, the head-mounted device may be implemented as a headset that includes an earpiece 106, an ear grip 104, one or more infrared sensors 102, and a light-emitting diode (LED) 108. The headset may be an over-the-ear headset or an earloop headset, in which earpiece 106 inside or over a user's ear canal and ear grip 104 looped around the outside of the user's ear. The headset may additionally allow the user to transmit and/or receive audio signals through earpiece 106, a microphone (not shown), and/or other input/output (I/O) devices. For example, the headset may be a Bluetooth (Bluetooth™ is a registered trademark of Bluetooth SIG, Inc.) headset that allows the user to place phone calls through a mobile phone paired with the headset and/or listen to music on the mobile phone. The headset may also allow the user to interact with the mobile phone through voice controls instead of using a keyboard and/or touch-sensitive display on the mobile phone.

The headset may be worn in a way that positions infrared sensors 102 in proximity to the user's eye. For example, the headset may be worn over the user's left ear so that infrared sensors 102 are located to the bottom and left of the user's left eye and are within approximately an inch of the user's left eye. Infrared sensors 102 may then be used to detect the user's eyelid and/or eye movements, which in turn may be used by a processor (not shown) in the headset to detect drowsiness in the user. Using infrared sensors to detect eyelid movements, eye movements, and drowsiness in users is described in further detail below with respect to FIGS. 2 and 3A-3D.

If drowsiness is detected based on the user's eyelid and/or eye movements, an alert may be generated on LED 108 and/or another output device in the headset. For example, LED 108 may flash if the user's level of alertness, as determined by the user's eyelid and/or eye movements, drops below a threshold. In a second example, an alarm may be played through earpiece 106 to provide an audio alert to the user. In a third example, a vibration motor (not shown) in the headset may be activated to provide a tactile alert to the user. The alerts described above may be used alone and/or in combination with one another to provide an effective mechanism for managing and reducing fatigue and drowsiness in the user.

Figure 2:
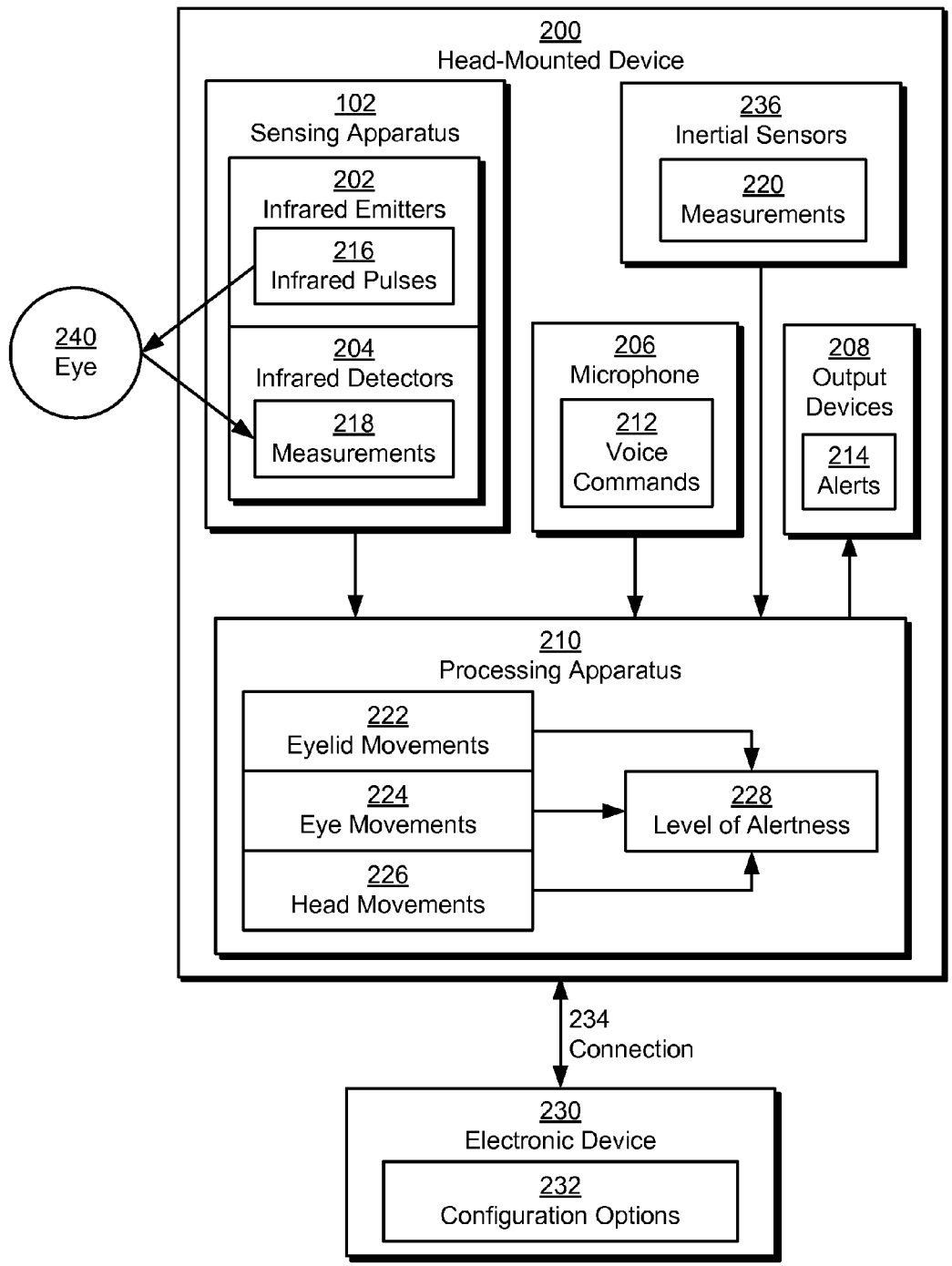
FIG. 2 shows a schematic of a head-mounted device in accordance with one or more embodiments.

FIG. 2 shows a schematic of a head-mounted device 200 in accordance with one or more embodiments. As described above, head-mounted device 200 may be a headset, such as the headset of FIG. 1. Alternatively, head-mounted device 200 may be built into other types of wearable devices and/or form factors, such as head-mounted displays, helmet-mounted devices, hat-mounted devices, eyeglasses, safety glasses, and/or eyewear devices.

Head-mounted device 200 may be paired with an electronic device 230. For example, head-mounted device 200 may use Bluetooth, near field communication (NFC), Wi-Fi Direct (Wi-Fi Direct™ is a registered trademark of Wi-Fi Alliance Corp.), and/or another wired or wireless connection 234 to establish communication with electronic device 230.

Once communication is established, a user may interact with electronic device 230 through head-mounted device 200 by providing one or more voice commands 212 through a microphone 206 on head-mounted device 200. For example, the user may speak voice commands 212 into microphone 206 to interact with a natural language user interface on a mobile phone, tablet computer, laptop computer, motor vehicle, navigation system, and/or other electronic device 230 to which head-mounted device 200 is paired. Head-mounted device 200 may relay voice commands 212 to electronic device 230 through connection 234, and electronic device 230 may generate visual, audio, and/or tactile output in response to voice commands 212. Alternatively, electronic device 230 may relay one or more commands in response to voice commands 212 to head-mounted device 200 through connection 234, and head-mounted device 200 may use one or more output devices 208 to generate output corresponding to the commands.

The user may also use connection 234 to configure the operation of head-mounted device 200 from electronic device 230. For example, the user may interact with a touchscreen, keyboard, set of buttons, and/or other input device on electronic device 230 to specify one or more configuration options 232 for head-mounted device 200. Configuration options 232 may be obtained using an application (e.g., a mobile application) in electronic device 230 and used by electronic device 230 and/or head-mounted device 200 to modify the behavior of head-mounted device 200. For example, configuration options 232 may be transmitted from electronic device 230 over connection 234 to head-mounted device 200, and head-mounted device 200 may process input from a sensing apparatus 102, a microphone 206, and/or other input device and/or generate output on output devices 208 based on configuration options 232. Conversely, configuration options 232 may be stored locally on electronic device 230 and used by electronic device 230 to modify the operation of head-mounted device 200. For example, electronic device 230 may use connection 234 to obtain input collected from input devices on head-mounted device 200, process the input based on configuration options 232, and/or generate output on electronic device 230 and/or head-mounted device 200 based on the processed input.

In one or more embodiments, head-mounted device 200 and/or electronic device 230 include functionality to detect and manage drowsiness in a user wearing head-mounted device 200. As shown in FIG. 2, sensing apparatus 102 in head-mounted device 200 may include a number of infrared emitters 202 that emit infrared pulses 216 at an eye 240 of the user. Sensing apparatus 102 may also include a number of infrared detectors 204 that produce measurements 218 of reflections of infrared pulses 216 from eye 240. For example, infrared emitters 202 and infrared detectors 204 may be positioned in proximity to the user's eye 240 while head-mounted device 200 is worn by the user.

Those skilled in the art will appreciate that measurements 218 of reflected infrared pulses 216 from eye 240 may vary with the surfaces from which infrared pulses 216 are reflected. First, measurements 218 of reflected infrared pulses 216 from the surface of eye 240 may be lower than measurements 218 of reflected infrared pulses 216 from the surface of an eyelid covering eye 240 (e.g., during a blink) because the diffuse surface of the eyelid promotes greater reflection of infrared pulses 216 than the smoother surface of eye 240. Second, a white part of eye 240 may reflect infrared pulses 216 more than the pupil, iris, and/or another colored part of eye 240, thus producing higher measurements 218 of reflected infrared pulses 216 than the colored part. Measurements 218 may thus fluctuate in response to blinks, saccades, and/or other eyelid movements 222 and/or eye movements 224 in the user.

In turn, changes in measurements 218 may be used by a processing apparatus 210 (e.g., a processor) in head-mounted device 200 and/or electronic device 230 to detect eyelid movements 222 and/or eye movements 224 in the user. However, measurements 218 made using an infrared sensor containing one infrared emitter and one infrared detector may lack directionality and be susceptible to noise and/or other factors that preclude accurate detection of eyelid movement 222 and eye movement 224. For example, an increase in measurements 218 made using one infrared emitter and one infrared detector may be caused by closing an eyelid over eye 240 (e.g., during the first half of a blink), an eye movement that increases reflection of infrared pulses 216 from the white part of eye 240 and decreases reflection of infrared pulses 216 from the colored part of eye 240, and/or a decrease in distance between the infrared sensor and eye 240. On the other hand, a decrease in measurements 218 made using one infrared emitter and one infrared detector may be caused by opening of the eyelid to reveal eye 240 (e.g., during the second half of a blink), an eye movement that increases reflection of infrared pulses 216 from the colored part of eye 240 and decreases reflection of infrared pulses 216 from the white part of eye 240, and/or an increase in distance between the infrared sensor and eye 240. Consequently, a given measurement or change across measurements 218 of reflected infrared pulses 216 from the infrared emitter by the infrared detector may be caused by one of multiple movements in eye 240 and/or head-mounted device 200, which cannot be distinguished from other movements without additional measurements from other infrared sensors.

In addition, measurements 218 from two infrared sensors (e.g., two infrared detectors 204 and one infrared emitter, two infrared emitters 202 and one infrared detector, etc.) may enable the detection of rough eye and/or eyelid movements but may lack information that enables the detection of movement along multiple axes. For example, two infrared sensors arranged vertically (e.g., with one sensor located above the other) may enable the detection of vertical eyelid movements because as the eyelid moves up and down over eye 240, one infrared sensor will measure a change in the reflected infrared pulses from eye 240 before the other infrared sensor. However, substantially horizontal eye movements and changes in distance between the infrared sensors and eye 240 may produce changes in measurements 218 from both infrared sensors at the same time and thus be indistinguishable from one another. Diagonal eye movements may additionally be difficult to distinguish from vertical eyelid movements using the vertically arranged infrared sensors.

Conversely, two infrared sensors arranged horizontally (e.g., with one sensor located to the side of the other) may enable the detection of horizontal eye movements because as eye 240 moves across the distance separating the infrared sensors, one infrared sensor will measure a change in the reflected infrared pulses from eye 240 before the other infrared sensor. On the other hand, the horizontally arranged infrared sensors may not be able to distinguish between vertical eyelid movements and changes in distance between the infrared sensors and eye 240, which trigger changes in measurements 218 from both infrared sensors at the same time.

In one or more embodiments, multiple infrared emitters 202 and/or infrared detectors 204 are used in head-mounted device 200 to increase the accuracy with which eyelid movement 222 and/or eye movement 224 are detected. Such infrared emitters 202 and/or infrared detectors 204 may be positioned along two axes so that substantially vertical eyelid movements can be distinguished from substantially horizontal eye movements.

For example, three or more infrared emitters 202 may be arranged in an L-shape, a triangular shape, and/or other polygonal shape in which at least two infrared emitters 202 are separated by a horizontal distance and at least two infrared emitters 202 are separated by a vertical distance. One or more infrared detectors 204 may then be placed within or near the polygonal shape, and infrared pulses 216 may be emitted from infrared emitters 202 in an alternating fashion (e.g., 1-millisecond (ms) pulses every 10 ms, separated by 3-ms intervals). Measurements 218 of reflected infrared pulses 216 may thus be read from different emitters 202 at different times 202, and the horizontal and vertical separation of infrared emitters 202 from one another may allow measurements 218 of reflected infrared pulses 216 to capture both vertical eyelid movements 222 and horizontal eye movements 224. Conversely, three or more infrared detectors 204 may be arranged in a similar polygonal shape, and one or more infrared emitters 202 may be used with infrared detectors 204 to make measurements 218 of reflected infrared pulses 216 that change with both horizontal eye movements 224 and vertical eyelid movements 222.

In another example, two infrared emitters 202 may be arranged along one axis, and two infrared detectors 204 may be arranged along another (e.g., orthogonal) axis. Infrared emitters 202 may flash infrared pulses 216 at eye 240 in an alternating fashion, and infrared detectors 204 may make measurements 218 of the reflected infrared pulses 216 from eye 240. The horizontal and vertical separation among infrared emitters 202 and infrared detectors 204 may thus enable the detection of horizontal eye movements 224, diagonal eye movements 224, and vertical eyelid movements 222. Layouts of infrared emitters and infrared detectors in head-mounted devices for detecting eyelid movements and eye movements in users are described in further detail below with respect to FIGS. 3A-3D.

As described above, measurements 218 of reflected infrared pulses 216 may be sent to processing apparatus 210 for use in detecting and characterizing eyelid movements 222 and/or eye movements 224 of the user. For example, processing apparatus 210 may use increases and decreases in measurements 218 associated with different infrared emitters 202 and/or infrared detectors 204 to identify the direction and speed of the user's eyelid movements 222 and eye movements 224.

Processing apparatus 210 may additionally characterize eyelid movements 222 by determining the values of one or more parameters associated with eyelid movements 222. For example, measurements 218 may track a blink by increasing from a minimum value to a maximum value while an eyelid is moving downward over eye 240, staying at the maximum value while eye 240 is closed, and decreasing from the maximum value to the minimum value while the eyelid moves upward to open eye 240. Processing apparatus 210 may use measurements 218 to determine, for the user, a blink rate (e.g., blinks/minute), blink duration (e.g., in ms), closing amplitude velocity ratio, opening amplitude velocity ratio, percentage of eyelid closure (PERCLOS), closing duration (e.g., time over which measurements 218 increase to the maximum value), closure duration (e.g., time in which measurements 218 stay at the maximum value), and/or reopening duration (e.g., time over which measurements 218 decrease from the maximum value to the minimum value).

Similarly, processing apparatus 210 may characterize eye movements 224 using one or more parameters associated with eye movements 224. For example, processing apparatus 210 may use increases and decreases in measurements 218 associated with saccades and/or other substantially horizontal eye movements 224 to determine the direction, amplitude, latency, peak velocity, duration, and/or other characteristics associated with eye movements 224.

Processing apparatus 210 may also obtain measurements 220 from one or more inertial sensors 236 in head-mounted device 200 and use measurements 220 to detect and characterize head movements 226 of the user. For example, processing apparatus 210 may obtain measurements 220 of acceleration and/or angular velocity in one or more axes from an accelerometer, gyroscope, and/or other inertial sensors 236 and use measurements 220 to detect changes in the user's head movements 226 over time. Processing apparatus 210 may also use measurements 220 to evaluate parameters associated with head movements 226 and/or the user's general motion, such as the speed of a vehicle driven by the user, the amount of time in which the user has been in a relatively stationary (e.g., sitting) position, and/or the user's level of activity.

Processing apparatus 210 may then combine eyelid movements 222, eye movements 224, and/or head movements 226 to determine a level of alertness 228 in the user. For example, processing apparatus 210 may analyze the characterized eyelid movements 222, eye movements 224, and/or head movements 226 to determine if the user is showing signs of drowsiness and/or inattentiveness. Signs of drowsiness may include, but are not limited to, slower blinks, blinks with longer closure durations, blinks with higher and/or more variable opening and closing amplitude velocity ratios, head rolling movements, and/or slower saccades. Signs of inattentiveness may include, but are not limited to, a head position and/or eye movement that indicates that the user's focus is on something other than the space in front of the user (e.g., during driving of a vehicle). Any signs of drowsiness or inattentiveness may then be used to calculate a numeric level of alertness 228. Alternatively, level of alertness 228 may include a number of metrics representing drowsiness, attentiveness, and/or other factors that may affect alertness in the user.

Determination of level of alertness 228 may additionally be calibrated to the user's individual eyelid movements 222, eye movements 224, and/or head movements 226. For example, processing apparatus 210 may track parameters associated with eyelid movements 222, eye movements 224, and/or head movements 226 over time to identify "normal" values of the parameters for the user. Deviation of the measurements from the normal values may then be identified by processing apparatus 210 as a change in level of alertness 228.

If level of alertness 228 drops below a threshold, processing apparatus 210 may generate one or more alerts 214 on one or more output devices 208 to increase level of alertness 228 and/or mitigate adverse effects associated with a reduced level of alertness 228, such as loss of productivity and/or accidents. Such alerts 214 may include audio alerts (e.g., alarms, music, voice calls), visual alerts (e.g., flashing of an LED), tactile alerts (e.g., vibration, electric stimulus), and/or other types of stimuli for increasing level of alertness 228. Alerts may also be generated on electronic device 230, in lieu of or in addition to alerts 214 on head-mounted device 200. For example, alerts on an external electronic device 230 may include vibrations generated by car seats, wristbands, and/or portable electronic devices; audio alerts on a portable electronic device, computer system, and/or navigation system; and/or visual alerts on a display, one or more LEDs, and/or one or more lights.

As mentioned above, the user may specify one or more configuration options 232 for head-mounted device 200 from electronic device 230. As a result, the user may configure the sensitivity of head-mounted device 200 to signs of drowsiness, inattentiveness, and/or other characteristics associated with reduced level of alertness 228. Similarly, the user may configure the generation of alerts 214 based on level of alertness 228, including the types of alerts 214 generated, the relative timing of alerts 214, configuration parameters for each alert (e.g., sound file to be played in an audio alarm, color of flashing light, pattern of vibration, etc.), and/or the strength or duration of each alert.

Figure 3A:
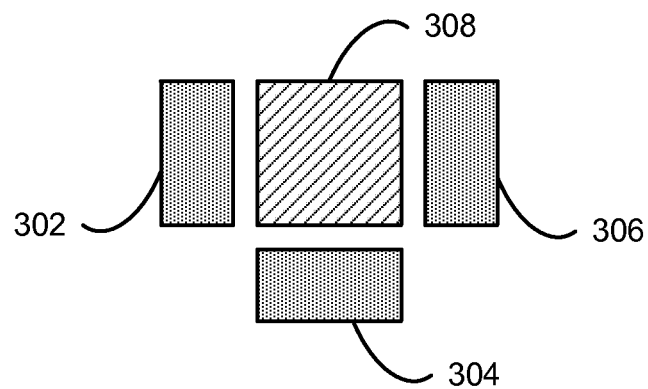
FIG. 3A shows an exemplary layout of a sensing apparatus in a head-mounted device in accordance with one or more embodiments.

FIG. 3A shows an exemplary layout of infrared sensors in a head-mounted device (e.g., head-mounted device 200 of FIG. 2) in accordance with one or more embodiments. As mentioned above, the infrared sensors may be placed in proximity to a user's eye and used to detect both substantially horizontal eye movements and substantially vertical eyelid movements from the user. As a result, the infrared sensors may be arranged along at least two axes to differentiate between horizontal and vertical movement.

The layout of FIG. 3A includes three infrared emitters 302-306 and one infrared detector 308. Infrared emitters 302 and 306 are positioned along a horizontal line, infrared detector 308 is located along the same horizontal line between infrared emitters 302 and 306, and infrared emitter 304 is positioned directly below infrared detector 308. Infrared emitters 302 and 306 may be separated by a horizontal distance, and infrared emitter 304 may be separated from infrared emitters 302 and 306 by a vertical distance. Infrared emitters 302-306 may thus be arranged in a triangular shape, and infrared detector 308 may be placed in the center of the triangular shape.

To enable detection of both horizontal eye movements and vertical eyelid movements, infrared emitters 302-306 may be configured to alternate emission of infrared pulses at an eye of a user. For example, each infrared emitter 302-306 may emit a 1-ms infrared pulse every 10 ms. Emission of infrared pulses from infrared emitters 302-306 may be staggered every 3 ms or so to allow infrared detector 308 to measure the reflected infrared pulses from each individual infrared emitter.

In turn, measurements of reflected infrared pulses from infrared emitters 302-306 may be obtained by infrared detector 308 and used to detect eye and eyelid movements in the user. As described above, the user's eyelid may reflect infrared pulses more than the user's eye, and the white part of the eye may reflect infrared pulses more than the colored part of the eye. A closing of the user's eye (e.g., during the first half of a blink) may thus be detected as an simultaneous increase in the measurements of reflected infrared pulses from infrared emitters 302 and 306, followed by a subsequent increase in the measurements of reflected infrared pulses from infrared emitter 304. An opening of the user's eye (e.g., during the second half of a blink) may be detected as a decrease in the measurements of reflected infrared pulses from infrared emitter 304, followed by a subsequent simultaneous decrease in the measurements of reflected infrared pulses from infrared emitters 302 and 306.

Saccades of the user's eye may also be detected as staggered decreases or increases in measurements from infrared emitters 302-306 along the horizontal axis. As the colored part of the eye shifts from left of the infrared sensors to over the infrared sensors, infrared detector 308 may measure a series of decreases in reflected infrared pulses from infrared emitter 302, then from infrared emitter 304, and finally from infrared emitter 306. As the colored part of the eye passes from over the infrared sensors to the right of the infrared sensors, infrared detector 308 may measure a series of increases in reflected infrared pulses from infrared emitter 302, then from infrared emitter 304, and finally from infrared emitter 306. As the colored part of the eye passes from right of the infrared sensors to over the infrared sensors, infrared detector 308 may measure a series of decreases in reflected infrared pulses from infrared emitter 306, then from infrared emitter 304, and finally from infrared emitter 302. As the colored part of the eye shifts from over the infrared sensors to left of the infrared sensors, infrared detector 308 may measure a series of increases in reflected infrared pulses from infrared emitter 306, then from infrared emitter 304, and finally from infrared emitter 302.

Those skilled in the art will appreciate that the layout of FIG. 3A may also be used with multiple infrared detectors and one infrared emitter. For example, three infrared detectors may be arranged in a triangular shape around a single infrared emitter. Three measurements of each reflected infrared pulse emitted by the infrared emitter may then be made by the infrared detectors in the same way that measurements of reflected infrared pulses from three different infrared emitters 302-306 are made by a single infrared detector 308. Staggered changes in the measurements across the horizontal and vertical axes may then be analyzed to detect horizontal eye movement and vertical eyelid movement, as described above.

Figure 3B:
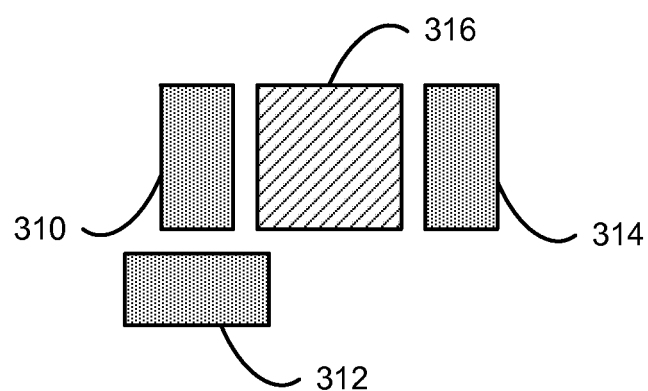
FIG. 3B shows an exemplary layout of a sensing apparatus in a head-mounted device in accordance with one or more embodiments.

FIG. 3B shows an exemplary layout of infrared sensors in a head-mounted device (e.g., head-mounted device 200 of FIG. 2) in accordance with one or more embodiments. As with the infrared sensors of FIG. 3A, the infrared sensors of FIG. 3B may be located in proximity to a user's eye and include three infrared emitters 310-314 and one infrared detector 316. In the layout of FIG. 3B, infrared emitters 310 and 314 may be arranged in a horizontal line, infrared detector 316 may be placed along the same horizontal line between infrared emitters 310 and 314, and infrared emitter 312 may be positioned directly below infrared emitter 310. As a result, infrared emitters 310-314 may form an L-shape, and infrared detector 316 may be placed roughly in the middle of the L-shape.

As with infrared emitters 302-306 of FIG. 3A, emission of infrared pulses from infrared emitters 310-314 may be performed in an alternating fashion so that reflected infrared pulses from each infrared emitter may be measured by infrared detector 316. Measurements from infrared detector 316 may then be used to detect vertical eyelid movement and horizontal eye movement in the user.

First, a closing of the user's eye (e.g., during the first half of a blink) may be detected as an simultaneous increase in measurements of reflected infrared pulses from infrared emitters 310 and 314, followed by a subsequent increase in measurements of reflected infrared pulses from infrared emitter 312. An opening of the user's eye (e.g., during the second half of a blink) may be detected as a decrease in measurements of reflected infrared pulses from infrared emitter 312, followed by a subsequent synchronous decrease in the measurements of reflected infrared pulses from infrared emitters 310 and 314.

Second, saccades of the user's eye may be detected as staggered decreases or increases in measurements along the horizontal axis of the layout. As the colored part of the eye shifts from left of the infrared sensors to over the infrared sensors, infrared detector 316 may measure a simultaneous decrease in the reflected infrared pulses from infrared emitters 310-312, followed by a decrease in the reflected infrared pulses from infrared emitter 314. As the colored part of the eye passes over the infrared sensors to the right of the infrared sensors, infrared detector 316 may measure a simultaneous increase in the reflected infrared pulses from infrared emitters 310-312, followed by an increase in the reflected infrared pulses from infrared emitter 314. As the colored part of the eye passes from right of the infrared sensors to over the infrared sensors, infrared detector 316 may measure a decrease in the reflected infrared pulses from infrared emitter 314, followed by a simultaneous decrease in the reflected infrared pulses from infrared emitters 310-312. As the colored part of the eye shifts from over the infrared sensors to left of the infrared sensors, infrared detector 316 may measure an increase in the reflected infrared pulses from infrared emitter 314, followed by a simultaneous increase in the reflected infrared pulses from infrared emitters 310-312.

The layout of FIG. 3B may also be implemented using three infrared detectors arranged in an L-shape and an infrared emitter placed in or near the center of the L-shape. Three measurements of each reflected infrared pulse emitted by the infrared emitter may be made by the infrared detectors in the same way that measurements of reflected infrared pulses from three different infrared emitters 310-314 are made by a single infrared detector 316. Staggered changes in the measurements along the horizontal and vertical axes may then be analyzed to detect horizontal eye movement and vertical eyelid movement, as discussed above.

Figure 3C:
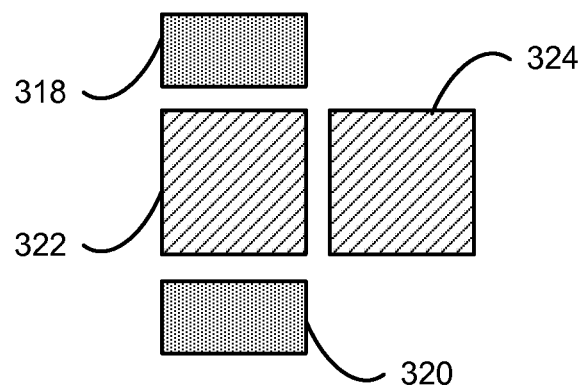
FIG. 3C shows an exemplary layout of a sensing apparatus in a head-mounted device in accordance with one or more embodiments.

FIG. 3C shows an exemplary layout of infrared sensors in a head-mounted device (e.g., head-mounted device 200 of FIG. 2) in accordance with one or more embodiments. The layout of FIG. 3C includes two infrared emitters 318-320 and two infrared detectors 322-324. Infrared emitters 318-320 are arranged along a vertical axis, infrared detector 322 is positioned along the same vertical axis between infrared emitters 318-320, and infrared detector 324 is positioned to the right of infrared detector 322.

As with the infrared sensors of FIGS. 3A-3B, the infrared sensors of FIG. 3C may be used to detect substantially vertical eyelid movements and substantially horizontal eye movements in a user. For example, infrared emitters 318-320 and infrared detectors 322-324 may be placed in proximity to the user's eye while the user wears a head-mounted device containing the infrared sensors. Infrared emitters 318-320 may be configured to alternate emission of infrared pulses at the user's eye (e.g., by staggering the pulses to occur 5 ms apart, 100 times a second), and infrared detectors 322-324 may measure reflections of the infrared pulses from the user's eye. Changes in the measured reflections over time may then be used to detect and characterize the user's eye and eyelid movements.

A closing of the user's eye (e.g., during the first half of a blink) may be detected as an increase in the measurements of both infrared detectors 322-324 of reflected infrared pulses from infrared emitter 318, followed by a subsequent increase in the measurements of both infrared detectors 322-324 of reflected infrared pulses from infrared emitter 320. An opening of the user's eye (e.g., during the second half of a blink) may be detected as a decrease in the measurements of both infrared detectors 322-324 of reflected infrared pulses from infrared emitter 320, followed by a subsequent decrease in the measurements of both infrared detectors 322-3224 of reflected infrared pulses from infrared emitter 318.

As the colored part of the eye shifts from left of the infrared sensors to over the infrared sensors, infrared detector 322 may measure a simultaneous decrease in the reflected infrared pulses from both infrared emitters 318-320, and infrared detector 322 may subsequently measure a simultaneous decrease in the reflected infrared pulses from both infrared emitters 318-320. As the colored part of the eye passes over the infrared sensors to the right of the infrared sensors, infrared detector 322 may measure a simultaneous increase in reflected infrared pulses from both infrared emitters 318-320, with infrared detector 322 measuring a subsequent simultaneous increase in reflected infrared pulses from both infrared emitters 318-320. As the colored part of the eye passes from right of the infrared sensors to over the infrared sensors, infrared detector 324 may measure a simultaneous decrease in the reflected infrared pulses from both infrared emitters 318-320, and infrared detector 322 may measure a subsequent simultaneous decrease in reflected infrared pulses from both infrared emitters 318-320. As the colored part of the eye shifts from over the infrared sensors to left of the infrared sensors, infrared detector 324 may measure a simultaneous increase in the reflected infrared pulses from both infrared emitters 318-320, and infrared detector 322 may measure a subsequent simultaneous increase in the measurement of reflected infrared pulses from both infrared emitters 310-312.

Figure 3D:
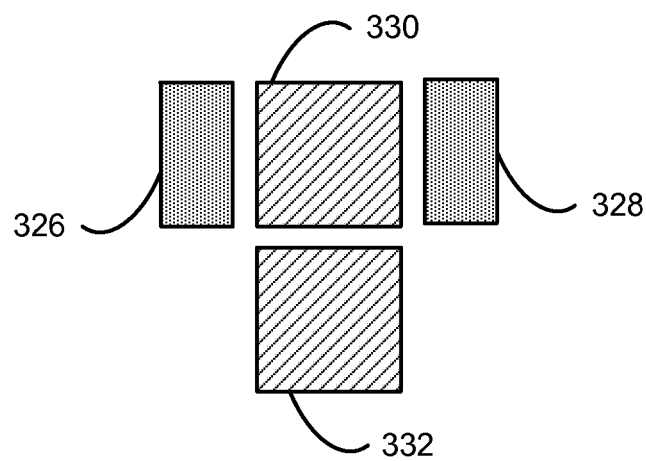
FIG. 3D shows an exemplary layout of a sensing apparatus in a head-mounted device in accordance with one or more embodiments.

FIG. 3D shows an exemplary layout of infrared sensors in a head-mounted device in accordance with one or more embodiments. Like the layout of FIG. 3C, the layout of FIG. 3D includes two infrared emitters 326-328 and two infrared detectors 330-332. Infrared detectors 330-332 are arranged along a vertical axis, and infrared emitters 326-328 are arranged along a horizontal axis on either side of infrared detector 330.

Infrared emitters 326-328 and infrared detectors 330-332 may be placed in proximity to a user's eye (e.g., while the user wears a head-mounted device containing the infrared sensors). Infrared emitters 326-328 may alternate emission of infrared pulses at the user's eye, and infrared detectors 330-332 may measure reflections of the infrared pulses from the user's eye. Changes in the measured reflections over time may then be used to detect and characterize the user's eye and eyelid movements.

A closing of the user's eye (e.g., during the first half of a blink) may be detected as a simultaneous increase in the measurement of reflected infrared pulses from both infrared emitters 326-328 by infrared detector 330, followed by a subsequent simultaneous increase in the measurement of reflected infrared pulses from both infrared emitters 326-328 by infrared detector 332. An opening of the user's eye (e.g., during the second half of a blink) may be detected as a simultaneous decrease in the measurement of reflected infrared pulses from both infrared emitters 326-328 by infrared detector 332, followed by a subsequent simultaneous decrease in the measurement of reflected infrared pulses from both infrared emitters 326-328 by infrared detector 330.

As the colored part of the eye shifts from left of the infrared sensors to over the infrared sensors, both infrared detectors 330-332 may simultaneously measure a decrease in reflected infrared pulses from infrared emitter 326, followed by a simultaneous decrease in measurements by both infrared detectors 330-332 of reflected infrared pulses from infrared emitter 328. As the colored part of the eye passes over the infrared sensors to the right of the infrared sensors, both infrared detectors 330-332 may simultaneously measure an increase in reflected infrared pulses from infrared emitter 326, and then simultaneously measure an increase in reflected infrared pulses from infrared emitter 328. As the colored part of the eye passes from right of the infrared sensors to over the infrared sensors, both infrared detectors 330-332 may simultaneously measure a decrease in the reflected infrared pulses from infrared emitter 328, and then simultaneously measure a decrease in reflected infrared pulses from infrared emitter 326. As the colored part of the eye shifts from over the infrared sensors to left of the infrared sensors, both infrared detectors 330-332 may simultaneously measure an increase in the reflected infrared pulses from infrared emitter 328, and then simultaneously measure an increase in the reflected infrared pulses from infrared emitter 326.

Those skilled in the art will appreciate that other layouts of infrared detectors and infrared emitters may be used to detect eye and eyelid movements. For example, a two-dimensional array of detectors and/or emitters may be used to perform fine-grained detection of eye and/or eyelid movements, including diagonal and/or rolling movements. Similarly, multiple infrared detectors and infrared emitters may be arranged so that a row of two or more infrared detectors is located above or below a row of two or more infrared emitters.

Figure 4:
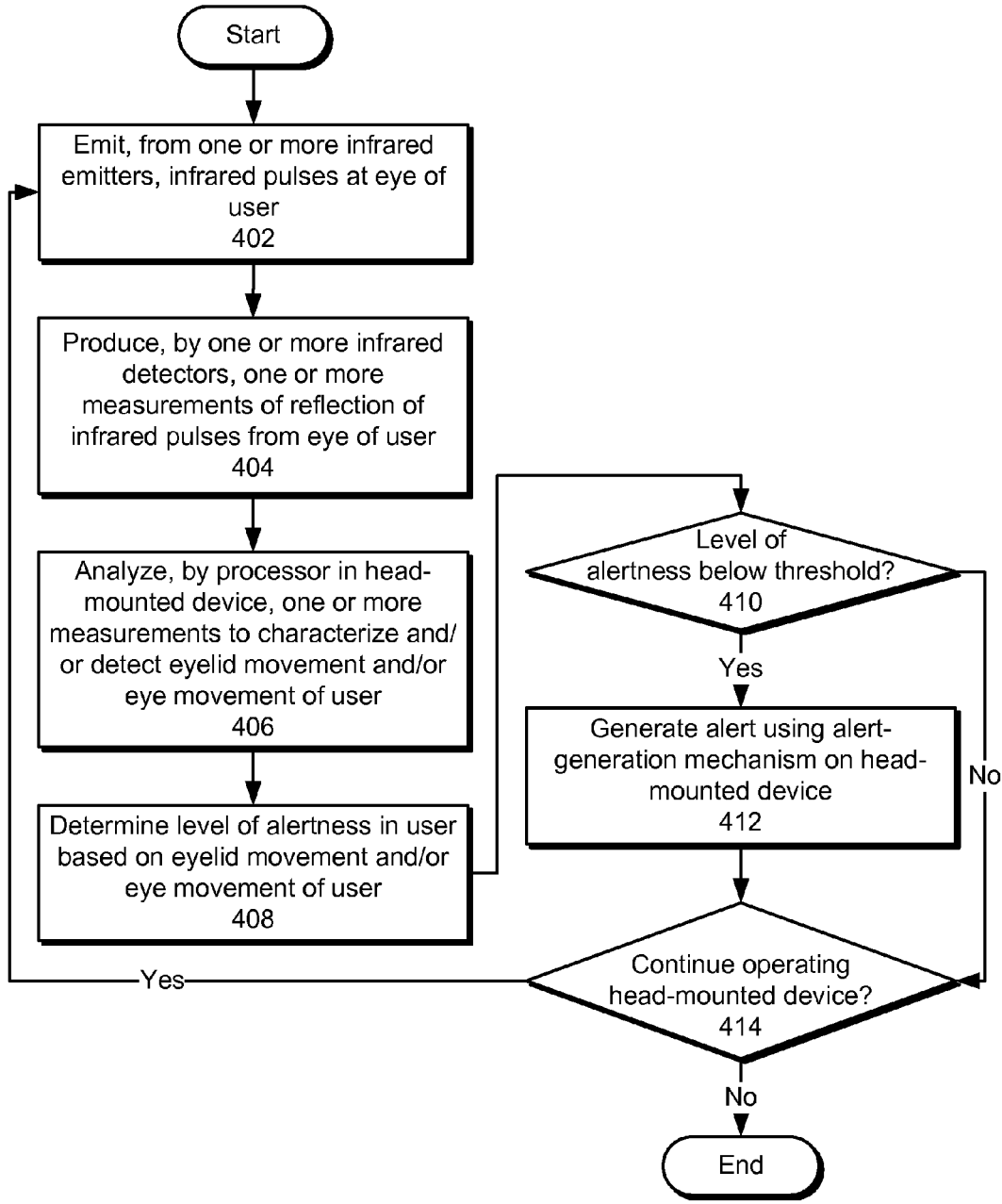
FIG. 4 shows a flowchart illustrating the process of operating a head-mounted device in accordance with one or more embodiments.

FIG. 4 shows a flowchart illustrating the process of operating a head-mounted device in accordance with one or more embodiments. In one or more embodiments, one or more of the steps may be omitted, repeated, and/or performed in a different order. Accordingly, the specific arrangement of steps shown in FIG. 4 should not be construed as limiting the scope of the embodiments.

As described above, the head-mounted device may include three or more infrared sensors containing one or more infrared emitters and one or more infrared detectors. During operation of the head-mounted device, infrared pulses are emitted from the infrared emitter(s) at an eye of a user (operation 402). For example, the infrared pulses may be emitted in an alternating fashion among two or more infrared emitters. If only one infrared emitter is used in the head-mounted device, the infrared emitter may emit the infrared pulses at regular intervals (e.g., every 10 ms).

Next, one or more measurements of the reflection of the infrared pulses from the eye of the user are produced by the infrared detector(s) (operation 404). The measurements may vary with the surfaces from which the infrared pulses are reflected. For example, measurements of infrared pulses reflected from the user's eyelid may be higher than measurements of infrared pulses reflected from the user's eye. Similarly, measurements of infrared pulses reflected from the white part of the eye may be higher than measurements of infrared pulses reflected from the colored part of the eye.

The measurements may then be analyzed by a processor in the head-mounted device to characterize and/or detect the user's eye and/or eyelid movements (operation 406). For example, staggered increases or decreases in measurements associated with horizontally and vertically separated infrared detectors and emitters may be used to detect and characterize substantially vertical eyelid movements and substantially horizontal eye movements in the user. To characterize the eye and/or eyelid movements, a number of parameters associated with the eye and/or eyelid movements may be determined. For example, the user's eyelid movements may be characterized using a blink rate, a blink duration, a closing amplitude velocity ratio, an opening amplitude velocity ratio, a percentage of eyelid closure (PERCLOS), a closing duration, a closure duration, and/or a reopening duration.

A level of alertness in the user is also determined based on the user's eyelid and/or eye movements (operation 408). For example, parameters associated with the user's eyelid and/or eye movements may be used to assess the user's overall level of alertness and/or rate the user's current state with respect to drowsiness, attentiveness, and/or other factors associated with alertness.

The user's level of alertness may drop below a threshold (operation 410). For example, the threshold may be a numeric threshold set by the user and/or the head-mounted device to represent given level of drowsiness and/or inattentiveness. If the user's level of alertness drops below the threshold, an alert is generated using an alert-generation mechanism on the head-mounted device (operation 412). The alert-generation mechanism may be an output device on the head-mounted device. The alert may include an audio alert, a visual alert, and/or a tactile alert. If the level of alertness does not drop below the threshold, generation of the alert may be skipped.

The head-mounted device may continue to be operated (operation 414) during use of the head-mounted device by the user. For example, the head-mounted device may be used to detect and manage drowsiness in the user while the head-mounted device is worn by the user. If the head-mounted device is to be operated, infrared sensors in the head-mounted device are operated to measure reflections of infrared pulses from the user's eye (operations 402-404), and the measurements are used by a processor in the head-mounted device to characterize and/or detect the user's eye and/or eyelid movements (operation 406). The eye and/or eyelid movements may then be used to determine the user's level of alertness (operation 408) and generate alerts if the level of alertness falls below a threshold (operations 410-412). Operation of the head-mounted device may thus continue until the head-mounted device is no longer worn by the user and/or is turned off by the user.

Figure 5:
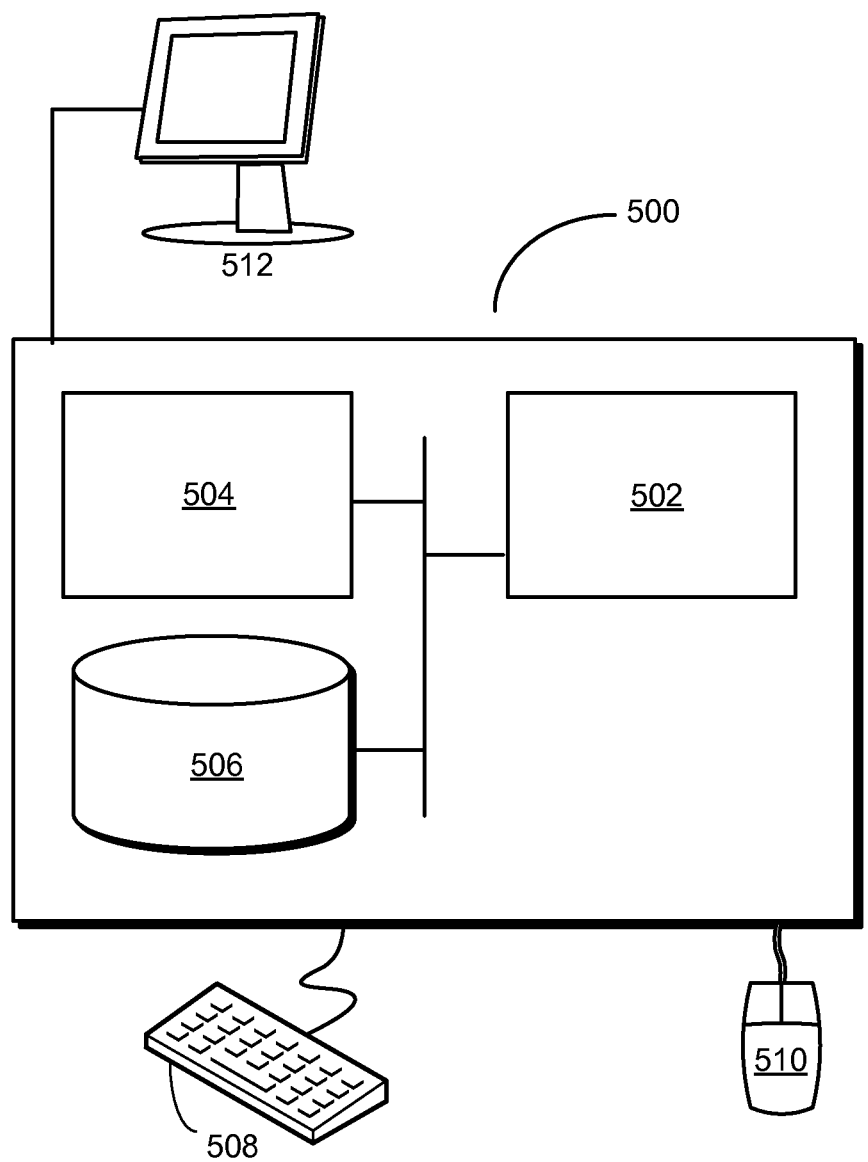
FIG. 5 shows a computer system in accordance with one or more embodiments.

FIG. 5 shows a computer system 500. Computer system 500 includes a processor 502, memory 504, storage 506, and/or other components found in electronic computing devices. Processor 502 may support parallel processing and/or multi-threaded operation with other processors in computer system 500. Computer system 500 may also include input/output (I/O) devices such as a keyboard 508, a mouse 510, and a display 512.

Computer system 500 may include functionality to execute various components of the present embodiments. In particular, computer system 500 may include an operating system (not shown) that coordinates the use of hardware and software resources on computer system 500, as well as one or more applications that perform specialized tasks for the user. To perform tasks for the user, applications may obtain the use of hardware resources on computer system 500 from the operating system, as well as interact with the user through a hardware and/or software framework provided by the operating system.

In one or more embodiments, computer system 500 provides a system for operating a head-mounted device such as a headset, head-mounted display, helmet-mounted device, hat-mounted device, eyeglasses, safety glasses, and/or eyewear device. The system may include a sensing apparatus containing one or more infrared emitters and one or more infrared detectors. The infrared emitters may emit infrared pulses at an eye of a user, and the infrared detectors may produce measurements of the reflected infrared pulses from the eye of the user. The infrared components (e.g., emitters and detectors) in the sensing apparatus may be separated from one another by horizontal and vertical distances.

The system may also include a processing apparatus that analyzes measurements from the infrared detector(s) to characterize and/or detect eye and eyelid movements of the user. For example, the processing apparatus may identifying a closing of the user's eyelid from an increase in the measurement of the reflected infrared pulses from a first infrared emitter, followed by an increase in the measurement of the reflected infrared pulses from a second infrared emitter positioned below the first infrared emitter. The processing apparatus may subsequently identify an opening of the user's eyelid from a decrease in the measurement of the reflected infrared pulses from the second infrared emitter, followed by a decrease in the measurement of the reflected infrared pulses from the first infrared emitter. The processing apparatus may characterize the eyelid movement using one or more parameters and determine a level of alertness in the user based on the characterized eyelid movement.

Finally, the system may include an alert-generation mechanism that generates an alert when the level of alertness in the user drops below a threshold. The alert may include an audio alert, a visual alert, a vibration, an action on a portable electronic device paired with the head-mounted device, an electrical stimulus, and/or a chemical stimulus.

In addition, one or more components of computer system 500 may be remotely located and connected to the other components over a network. Portions of the present embodiments (e.g., infrared emitters, infrared detectors, processing apparatus, etc.) may also be located on different nodes of a distributed system that implements the embodiments. For example, the present embodiments may be implemented using a cloud computing system that is connected to a remote head-mounted device worn by a user. The cloud computing system may process measurements of reflections of infrared pulses from the head-mounted device to characterize the user's eyelid and/or eye movements, determine the user's level of alertness based on the characterized movements, and generate alerts when the level of alertness drops below a threshold.

Although the disclosed embodiments have been described with respect to a limited number of embodiments, those skilled in the art, having benefit of this disclosure, will appreciate that many modifications and changes may be made without departing from the spirit and scope of the disclosed embodiments. Accordingly, the above disclosure is to be regarded in an illustrative rather than a restrictive sense. The scope of the embodiments is defined by the appended claims.

What is claimed is:

1. A head-mounted device, comprising:
a sensing apparatus, comprising:
a first infrared emitter and a second infrared emitter positioned below the first infrared emitter, wherein the first and second infrared emitters are configured to alternate emission of infrared pulses at an eye of a user; and
a first infrared detector configured to:
produce, at a first time, a first measurement of a reflection of the infrared pulses transmitted from the first infrared emitter to the eye of the user; and
produce, at a second time subsequent to the first time, a second measurement of the reflection of the infrared pulses transmitted from the second infrared emitter to the eye of the user; and a processing apparatus configured to analyze the first and second measurements from the first infrared detector to characterize an eyelid movement of the user.

2. The head-mounted device of claim 1, wherein:

the sensing apparatus further comprises a third infrared emitter positioned to a side of the first or second infrared emitters, wherein the third infrared emitter is configured to alternate emission of the infrared pulses with the first and second infrared emitters;

the first infrared detector is configured to produce, at a third time that is different from the first and second times, a third measurement of the reflection of the infrared pulses transmitted from the third infrared emitter to the eye of the user; and the processing apparatus is further configured to analyze the first, second, and third measurements to detect a saccade in an eye movement of the user.

3. The method of claim 1, wherein:

the sensing apparatus further comprises a second infrared detector positioned to a side of the first infrared detector;

the second infrared detector is configured to produce a third measurement of the reflection of the infrared signal from the eye of the user; and the processing apparatus is further configured to analyze the first, second, and third measurements to detect a saccade in an eye movement of the user.

4. The head-mounted device of claim 1, wherein the processing apparatus is further configured to:

determine a level of alertness in the user based on the characterized eyelid movement of the user.

5. The head-mounted device of claim 4, further comprising:

an alert-generation mechanism configured to generate an alert when the level of the alertness in the user drops below a threshold.

6. The head-mounted device of claim 5, wherein the alert comprises at least one of:

an audio alert;
a visual alert;
a vibration;
an action on a portable electronic device paired with the head-mounted device;
an electrical stimulus; and
a chemical stimulus.

7. The head-mounted device of claim 1, wherein the characterized eyelid movement comprises at least one of:

a blink rate;
a blink duration;
a closing amplitude velocity ratio;
an opening amplitude velocity ratio;
a percentage of eyelid closure (PERCLOS);
a closing duration;
a closure duration; and
a reopening duration.

8. The head-mounted device of claim 1, wherein analyzing the first and second measurements from the first infrared detector to characterize the eyelid movement of the user comprises:

identifying a closing of the eyelid of the user from an increase in the first measurement of the reflected infrared pulses from the first infrared emitter, followed by an increase in the second measurement of the reflected infrared pulses from the second infrared emitter; and identifying an opening of the eyelid of the user from a decrease in the second measurement of the reflected infrared pulses from the second infrared emitter, followed by a decrease in the first measurement of the reflected infrared pulses from the first infrared emitter.

9. The head-mounted device of claim 1, wherein the head-mounted device is at least one of:

a headset;
a head-mounted display;
a helmet-mounted device;
a hat-mounted device;
eyeglasses;
safety glasses; and
an eyewear device.

10. A head-mounted device, comprising:

a sensing apparatus, comprising:

a first infrared emitter configured to emit infrared pulses at an eye of a user;

a second infrared emitter positioned along a first axis with the first infrared emitter, wherein the first and second infrared emitters are configured to alternate emission of infrared pulses at the eye of the user;

a first infrared detector configured to:

produce, at a first time, a first measurement of a reflection of the infrared pulses transmitted from the first infrared emitter to the eye of the user; and produce, at a second time subsequent to the first time, a second measurement of the reflection of the infrared pulses transmitted from the second infrared emitter to the eye of the user; and a second infrared detector positioned, with the first infrared detector, along a second axis that is orthogonal to the first axis, wherein the second infrared detector is configured to:

produce a third measurement of the reflection of the infrared pulses transmitted from the first infrared emitter to the eye of the user; and produce a fourth measurement of the reflection of the infrared pulses transmitted from the second infrared emitter to the eye of the user; and a processing apparatus configured to analyze the first second, third, and fourth measurements from the first and second infrared detectors to characterize an eyelid movement and an eye movement of the user.

11. The head-mounted device of claim 10, wherein:

the processing apparatus is further configured to determine a level of alertness in the user based on the characterized eyelid movement of the user; and the head-mounted device further comprises an alert-generation mechanism configured to generate an alert when the level of the alertness in the user drops below a threshold.

12. A method, comprising:

operating, in a head-mounted device, three or more infrared components comprising a first infrared emitter, a second infrared emitter positioned along a first axis with the first infrared emitter, and one or more infrared detectors, wherein operating the three or more infrared components comprises:

emitting, from the first and second infrared emitters, infrared pulses in an alternating fashion at an eye of a user; and producing, by the one or more infrared detectors:

a first measurement of a reflection of the infrared pulses transmitted from the first infrared emitter to the eye of the user; and a second measurement of the reflection of the infrared pulses transmitted from the second infrared emitter to the eye of the user; and analyzing, by a processor in the head-mounted device, the first and second measurements to characterize an eyelid movement of the user.

13. The method of claim 12, further comprising:

determining, by the processor, a level of alertness in the user based on the characterized eyelid movement of the user; and generating, by an alert-generation mechanism on the head-mounted device, an alert when the level of the alertness in the user drops below a threshold.

14. The method of claim 12, wherein the three or more infrared components further comprise:

a third infrared emitter positioned outside of the first axis, wherein the third infrared emitter is configured to alternate emission of the infrared pulses with the first and second infrared emitters.

15. The method of claim 14, further comprising:

producing, by the one or more infrared detectors, a third measurement of the reflection of the infrared pulses transmitted from the third infrared emitter to the eye of the user; and analyzing, by the processor, the first, second, and third measurements to detect a saccade in an eye movement of the user.

16. The method of claim 12, wherein the three or more infrared components further comprise:

a second infrared detector positioned along a second axis with the first infrared detector, wherein the second axis is orthogonal to the first axis.

17. The method of claim 12, wherein the characterized eyelid movement comprises at least one of:

a blink rate;
a blink duration;
a closing amplitude velocity ratio;
an opening amplitude velocity ratio;
a percentage of eyelid closure (PERCLOS);
a closing duration;
a closure duration; and
a reopening duration.

18. The head-mounted device of claim 1, further comprising:

a microphone;
an output device; and
an inertial sensor.

19. The method of claim 13, further comprising:

calibrating the level of alertness based on the characterized eyelid movement of the user.

20. The method of claim 13, further comprising:

receiving, from an electronic device, one or more configuration options for the head-mounted device; and using the one or more configuration options to configure generation of the alert by the alert-generation mechanism.

* * * * *